United States Patent
Do-Yoo

(10) Patent No.: US 6,844,356 B2
(45) Date of Patent: Jan. 18, 2005

(54) HEMORRHOID THERAPEUTIC TREATMENT

(76) Inventor: Young Hee Do-Yoo, 6735 Fair Oaks Blvd., #11, Carmichael, CA (US) 95608

( * ) Notice: Subject to any disclaimer, the term of this patent is extended or adjusted under 35 U.S.C. 154(b) by 0 days.

(21) Appl. No.: 10/374,377

(22) Filed: Feb. 26, 2003

(65) Prior Publication Data

US 2004/0167159 A1 Aug. 26, 2004

(51) Int. Cl.$^7$ ........................ A61K 31/44; A61K 31/125
(52) U.S. Cl. ........................................ 514/305; 514/692
(58) Field of Search .................................. 514/305, 692

(56) References Cited

U.S. PATENT DOCUMENTS

| | | | | | |
|---|---|---|---|---|---|
| 1,526,633 A | * | 2/1925 | Gams | ........................ | 514/270 |
| 2,289,050 A | * | 7/1942 | Schnider | ..................... | 514/271 |
| 5,069,898 A | * | 12/1991 | Goldberg | ................. | 424/70.13 |

OTHER PUBLICATIONS

Gal–Fuzy et al., Pharmazie (1984), 39(8), 558–9 (HCA-PLUS Abstract No. 1985:32134).*

Hassler et al., Journal of the American Pharm. Association, Practical Pharmacy Edition (1953), 14, 26–7, 54 (ABSTRACT).*

Ferraris, Bollettino Chimico Farmaceutico (1939), 78, 173–6 (HCAPLUS Abstract No. 1939:52246).*

* cited by examiner

*Primary Examiner*—Raymond J. Henley, III
(74) *Attorney, Agent, or Firm*—Mark C. Jacobs

(57) ABSTRACT

A water solution of a mixture of quinine and camphor in preferably a ratio of 2 parts quinine to 1 part camphor is injected into hemorrhoidal tissue to effectuate a cure of the hemorrhoid. After a period of time, dependent upon the age and other aspects of the physical condition of the patient, the hemorrhoid will turn black, shrivel and flake off to yield a clean non-hemorrhoid area surrounding the anus.

10 Claims, No Drawings

HEMORRHOID THERAPEUTIC TREATMENT

FIELD OF THE INVENTION

This invention pertains to a chemical treatment of body tissue to rid the body of hemorrhoids using a novel composition.

BACKGROUND OF THE INVENTION

Hemorrhoids—a.k.a. piles, consist of a mass formed by the distention of the veins under the mucous membrane that lines the anal channel. These veins in essence lie under the skin that forms the external portion of the anus. It can be said that a hemorrhoid is related to varicose veins. A hemorrhoid may develop from an anal infection or from an increase in intra-abdominal pressure such as might take place during the course of pregnancy or while lifting heavy objects. Hemorrhoids may also arise if one strains to defecate and/or from complications of certain diseases. The weakness in the vein's wall permits the defect to develop. Mild hemorrhoids can be removed or may be treated by suppositories and/or nonirritating laxatives. Sometimes it is necessary to surgically remove the hemorrhoid.

Many over-the-counter remedies provide short-term relief from hemorrhoids. They do not however provide permanent relief. This invention relates to a chemical treatment to rid the body of hemorrhoid(s), as opposed to surgery. This invention does provide permanent relief that will last for years.

This patent application relates to the chemical composition and process of using these formulations for the removal of hemorrhoidal tissue.

Camphor, whose formula is $C_{10}H_{16}O$, is a ketone that occurs naturally in the wood of the camphor tree and is known to be useful as a topical application to relieve pain. It has been applied topically as an analgesic and antipruritic. It is well known to use camphor as a rub to treat respiratory diseases that involve mucous inflammations. Other topical uses and its use as an oral expectorant have also been documented.

Quinine, whose formula is $C_{20}H_{24}N_2O_2\text{-}3H_2O$, is a white amorphous powder or crystalline alkaloid that is both water and alcohol soluble. The preparation of quinine from ground cinchona bark using a lime and hot paraffin oil extraction system followed by a dilute sulfuric acid treatment and neutralization to yield quinine sulfate, which in turn is treated with ammonia to yield the alkaloid quinine is well known in the art. The use of quinine both orally and topically has been documented. Topically cinchona has been used as an astringent in eye solutions to combat infection. Its bacterial and anesthetic efforts led to it being used early on for malaria caused by the bite of the anopheles mosquito, and derivatives of quinine are used in tonic beverages.

In the instant invention, these two ingredients are used neither topically nor orally, but rather as the basis for an injectable solution for hemorrhoid relief The formulation of this invention is used not just to relieve the pain and irritation of hemorrhoids, but to completely rid the body of the hemorrhoid(s).

BRIEF DESCRIPTION OF THE FIGURES

There are no FIGURES in this application.

SUMMARY OF THE INVENTION

A chemical treatment for the permanent relief of hemorrhoids is provided by the chemical composition of this invention. The composition comprises a mixture of Yong Noe, a Chinese herb known to Western man as camphor, quinine, and distilled water. These two ingredients are ground into powder and dissolved in distilled water. The composition is then injected by a medical practitioner into the affected area at least once, and perhaps several times, over a two week period. After a period of time, the hemorrhoidal tissue will turn dark, harden, and flake off leaving the skin clear at the site of the former hemorrhoid.

It is a first object to provide a process for the chemical removal of hemorrhoids.

It is a second object to provide a chemical composition that can be injected into the hemorrhoidal tissue and cause the hemorrhoid to shrivel and disappear.

It is a third object to provide a procedure to cause hemorrhoids to disappear within a two to three week period subsequent to treatment.

Other objects of the invention will in part be obvious and will in part appear hereinafter.

The invention accordingly comprises the features, properties, and the relation of components of the instant composition, and the process of using the composition, which are exemplified in the following detailed disclosure, and the scope of the application of which will be indicated in the appended claims.

For a fuller understanding of the nature and objects of the invention reference should be made to the following detailed description.

DESCRIPTION OF THE PREFERRED EMBODIMENT

Camphor whose Latin name is *Cinnamomum camphora*, and is scientifically known as Dryobalanops aromatica Gaertn; and quinine (Cinchona) are the two primary ingredients of the formulation of this invention. They are used together in a water solution for injection into the irritated hemorrhoidal tissue to cause the hemorrhoid to contract, flake off, and disappear.

Applicant, who is an instructor at the Academy of Chinese Culture and Health Medicine, is a licensed acupuncturist and is an OMD, who practices Chinese medicine in this country. She has discovered a water solution of a specific ratio of these two ingredients when injected into the hemorrhoid, will cause the hemorrhoid to shrink and disappear.

Chinese medicine books have indicated that quinine alone can be used as a topical agent for the relief of the pain from hemorrhoids, but these books do not indicate that quinine can be used as an injectable solution to cure a person of hemorrhoids.

Applicant has found that when quinine alone is used as an injectable with water, the results are not effectual. The outer surface hardens, but the interior of the hemorrhoid is still very raw and thus painful. The analogy is made to the searing of a steak on a very hot pan. The surface is done, but the interior is still red and raw. Camphor, which is only slightly soluble in water, is believed to be too much of an irritant to the body to be capable for injection use alone.

Accordingly, to both Chinese and Western medicine, there are five types of hemorrhoids. The invention of this application has been found to work and cause full relief in four of five different types of hemorrhoidal tissue. They are: 1) Internal hemorrhoids; 2) External hemorrhoids; 3) Internal side of anus hemorrhoids, clumps of hemorrhoids; 4) Prolapse of the anus; but not type 5) Anal fistula. The reason for the ineffectiveness on the fifth type of hemorrhoid is that the anal fistula, which is one of the five types of hemorrhoids, can possibly be treated if it has developed near the anus and has shallow penetration in the surface skin. However, if the anal fistula has developed deep inside the skin tissue, penetrating close to the bones or the intestines, treatment is very difficult. Further studies are necessary to ascertain treatment efficaciously.

If a patient has more than one of the 1–4 types hemorrhoids, applicant has found it is better to treat only one area at a time to avoid anxiety in the patient.

It has been found that generally after 10–14 days have elapsed, after the second treatment (injection) the hemorrhoidal area will have disappeared. The treated area first turns black, hardens and then scales and flakes off. No scar tissue is formed and permanent relief is achieved. In some instances, a third treatment generally a week later, has been needed and in no instance has it taken more than four weeks to achieve the desired result.

Unlike creams or ointments, which give short-term pain relief, the treatment of this invention provides permanent relief and removal of the hemorrhoidal tissue.

In order to ensure efficiency of the treatment, the patient is advised to refrain from the consumption of alcohol and/or beverages containing alcohol during the period of treatment.

COMPOSITION

This patent application relates to the chemical composition comprising an intimate mixture of camphor and quinine dissolved in a water solution, and to the process of using this formulation for the removal of hemorrhoidal tissue.

In the instant invention, Camphor, whose chemical formula is $C_{10}H_{16}O$, and Quinine, whose chemical formula is $C_{20}H_{24}N_2O_2 \cdot 3H_2O$, are the two ingredients both of which have been used separately either topically or orally, and are now newly combined as the basis for an injectable solution for the permanent relief of hemorrhoids. The formulation of this invention is used not just to relieve the pain and irritation of hemorrhoids, but to completely rid the body of the hemorrhoids.

Camphor—whose scientific name is *Cinnamomum camphora*, and quinine (Cinchona) are two of the primary ingredients of the formulation of this invention. They are used together in a water solution for injection into the irritated tissue to cause the tissue to contract, flake off, and disappear.

Yong Noe, the first ingredient, is a Korean herb which in Western culture, is referred to as Camphor. The Young Noe is harvested, dried and ground with a mortar and pestle to yield a white flaky powder. In the alterative, after purchased as a powder, it is ground further to a very fine powder using a mortar and pestle. No determination of particle size was made.

The second ingredient is quinine. This is a bitter crystal alkaloid extracted from cinchona bark. It has the formula $C_{20}H_{24}N_2O_2$.

The third ingredient is distilled water. The Camphor and quinine are preferably mixed in a ratio within the range of 1 part of Camphor to 3 parts of quinine down to 1 part of each ingredient prior to dissolving them in the distilled water. The preferred ratio, as determined by experimentation is a 1:2 ratio of camphor to quinine. At the 1:2 ratio, patients exhibited little pain and relief was achievable in the shortest period of time for any similar case. When extra quinine was added to the formulation, the patient felt pain for the week following injection, but not to the degree prior to treatment. When less than a 1:1 ratio of dry ingredients were used, the hemorrhoid took more time to shrink and disappear. Also when less than a 1:1 ratio is used, pain was felt by the patient. If less water is used in making the solution, the weighed out portion will not dissolve.

No side effects from these treatments have been observed, and the composition is not toxic to adjacent skin. The color change observed is that the tissue goes from sore inflamed red, to gray, to black, and then scales or falls off leaving the skin clear. During the period subsequent to injection, pus is secreted from the treated area, which is easily removed by swabbing with alcohol or water to keep the treated area clean. This oozing commences within 3–4 days of the first treatment.

EXAMPLE 1

A mixture of Yong Noe and quinine in a 1:1 mixture in an amount of 37.5 grams are divided into 7 equal weight portions. Each portion of the mixture is dissolved in 4 grams of water by placing the composition in a container in boiling water for 3–5 minutes. The composition is a clear whitish solution. This solution is used at room temperature as the medicament for the treatment of hemorrhoids as will be discussed infra.

EXAMPLE 2

A mixture of camphor and quinine in a ratio of 2 parts quinine to 1 part camphor was prepared as in Example 1 and dissolved in 4 grams of distilled water to yield an amount of the composition of this invention for one injection.

Preferred Formulation 1 part camphor and 2 parts of quinine are intimately mixed to yield a composition having 37.5 grams of solids. The composition of 37.5 grams of solids is comprised of 25 grams of quinine and 12.5 grams of camphor. This mixture is equally divided and filled into seven different 10 cc vials, and 4 cc distilled water is added to each vial. Vials containing the composition of quinine, camphor, and the distilled water are heated in the boiling water in a metal container for 3–5 minutes. After 3–5 minutes of heating, only the dissolved liquid is extracted from each vial and used for the hemorrhoid treatment.

MODE OF TREATMENT

Typical Treatment Session

Step 1. An examination of the condition of the patient is conducted, to determine the patient's health, e.g., blood pressure, pulse, tongue discoloration, etc. The patient is then asked to comfortably lie on one side on top of the examination table for examination of the hemorrhoid. This position makes both the practitioner and the patient feel most comfortable.

Step 2. After carefully examining the hemorrhoid(s), a determination of the condition and the type is made. When a patient has a few hemorrhoids, treatment of the most painful one is carried out first, or; the tissue protrusion that a patient complains most about because of the associated pain is treated first.

Step 3. After injection into the hemorrhoid protrusion, the impacted area appears to slightly expand and harden, turning a gray or darkish color; however, the change is not consistent. After a single injection, in 3–4 days, the treated area starts to ooze. In approximately 7 days, the size of the injected area is reduced, forms clefs, and emits an offensive smell. As a result of the injection, this procedure, the treated hemorrhoid shrinks entirely without pain, and separates from the treated area. A patient is asked to return for follow-ups on a weekly basis until the hemorrhoid is completely cured. The skin surface will, after healing, have gone from black and grey, back to the normal skin tone of the person.

Efficacy of this Hemorrhoid Medication

Applicant would like to draw special attention to the fact that when an injection of the newly developed hemorrhoid medication is administered only into the hemorrhoid protrusion. The medication penetrates into the infested or affected area only, and not into surrounding tissue. Therefore, when the infested hemorrhoid protrusion is filled with this medication, the remnant of the medication starts to overflow without disturbing the surrounding tissue. The duration of complete recovery of treatment differs slightly depending on the patient's age, physical condition, and skin's elasticity. Patients between the ages of 20–40 take approximately 10–14 days whereas patients between the ages of 50 and up take approximately 14–21 days on average to cure.

Since certain changes maybe made in the described composition and the method of using the composition without departing from the scope of the invention herein involved, it is intended that all matter contained in the above description shall be interpreted as illustrative and not in a limiting sense.

I claim:

1. An injectable composition for the treatment of human hemorrhoids which consists essentially of a water solution quinine and camphor.

2. The composition of claim 1, wherein the ratio of quinine to camphor is in the range of 3 parts quinine: 1 part camphor, to 1 part quinine to 1 part camphor.

3. The composition of claim 1, wherein the ratio of quinine to camphor is about 2:1.

4. A bulk composition for division into seven similar injection treatments of human hemorrhoids which consists essentially of a ratio of 2 parts quinine to 1 part camphor in the amount of 37.5 grams of solids, dissolved in 28 grams of distilled water, resulting in 70 cc of solution.

5. A single injection for the treatment of human hemorrhoids consisting essentially of 10 cc of the bulk composition of claim 4.

6. The single injection of claim 5 wherein the injection consists essentially of 5.5 grams of dissolved solids in 4 grams of water.

7. A process for treating human hemorrhoids which comprises preparing a water solution of quinine and camphor, and injecting the solution into the hemorrhoidal tissue.

8. The process of claim 7, wherein the ingredients are subjected to heat to achieve maximum solubility prior to injection.

9. The process of claim 7, wherein the composition injected has a quinine to camphor ratio of 2:1.

10. The process of claim 7 wherein the composition injected has a quinine to camphor ratio of 3:1.

* * * * *